(12) United States Patent
Garth et al.

(10) Patent No.: US 9,414,956 B2
(45) Date of Patent: Aug. 16, 2016

(54) CERVICAL COLLAR SPINAL HEIGHT ADJUSTMENT SYSTEM

(71) Applicants: Geoffrey Garth, Long Beach, CA (US); Steven R. Burke, Huntington Beach, CA (US)

(72) Inventors: Geoffrey Garth, Long Beach, CA (US); Steven R. Burke, Huntington Beach, CA (US)

(73) Assignee: Aspen Medical Products, Inc., Irvine, CA (US)

(*) Notice: Subject to any disclaimer, the term of this patent is extended or adjusted under 35 U.S.C. 154(b) by 217 days.

(21) Appl. No.: 13/768,502

(22) Filed: Feb. 15, 2013

(65) Prior Publication Data

US 2013/0261519 A1 Oct. 3, 2013

Related U.S. Application Data

(60) Provisional application No. 61/619,175, filed on Apr. 2, 2012.

(51) Int. Cl.
*A61F 5/055* (2006.01)

(52) U.S. Cl.
CPC ........................ *A61F 5/055* (2013.01)

(58) Field of Classification Search
USPC ................. 602/17–19; 128/DIG. 23
See application file for complete search history.

(56) References Cited

U.S. PATENT DOCUMENTS

| | | | |
|---|---|---|---|
| 2,820,455 A * | 1/1958 | Hall | 602/18 |
| 2,904,040 A | 9/1959 | Hale | |
| 3,220,406 A | 11/1965 | Connelly | |
| 3,957,040 A * | 5/1976 | Calabrese | 602/36 |
| 4,628,913 A | 12/1986 | Lerman | |
| 4,951,655 A | 8/1990 | MacMillan | |
| 5,005,563 A * | 4/1991 | Veale | 602/18 |
| 5,010,881 A * | 4/1991 | Boudreau et al. | 602/19 |
| 5,531,669 A | 7/1996 | Varnau | |
| 5,624,387 A * | 4/1997 | McGuinness | 602/18 |
| 5,964,722 A * | 10/1999 | Goralnik et al. | 602/18 |
| 6,267,741 B1 * | 7/2001 | Lerman | 602/18 |
| 6,733,469 B2 * | 5/2004 | Miyaji et al. | 602/18 |
| 6,921,376 B2 | 7/2005 | Tweardy | |
| 7,371,222 B2 | 5/2008 | Heinz | |
| 7,549,970 B2 | 6/2009 | Tweardy | |
| 7,608,052 B1 * | 10/2009 | Baker | A61F 5/055 128/DIG. 23 |
| 7,846,117 B2 | 12/2010 | Leatt | |
| 8,038,635 B2 | 10/2011 | Dellanno | |
| 2008/0004556 A1 | 1/2008 | Gehlbach | |
| 2009/0149788 A1 * | 6/2009 | Dellanno | 602/18 |
| 2009/0247918 A1 | 10/2009 | Patron | |
| 2010/0185130 A1 | 7/2010 | Patron | |

FOREIGN PATENT DOCUMENTS

EP 2117481 B1 11/2011
WO WO2008050307 A1 5/2008

* cited by examiner

*Primary Examiner* — Ophelia A Hawthorne

(74) *Attorney, Agent, or Firm* — Fish & Tsang LLP

(57) ABSTRACT

Neck braces having versatile rear braces are provided. Some rear braces comprise various components including a rear panel having notches, a height adjustment mechanism, and at least one occipital lobe support. Each component can be movably attached to another component via a fastener (e.g., ball snap, snap connector, etc.), thereby allowing one component to rotate, tilt or otherwise move in relation to the other component.

20 Claims, 8 Drawing Sheets

CERVICAL COLLAR SPINAL HEIGHT ADJUSTMENT SYSTEM

This application claims the benefit of priority to U.S. Provisional Application No. 61/619,175, filed on Apr. 2, 2012. This and all other extrinsic materials discussed herein are incorporated by reference in their entirety. Where a definition or use of a term in an incorporated reference is inconsistent or contrary to the definition of that term provided herein, the definition of that term provided herein applies and the definition of that term in the reference does not apply.

FIELD OF THE INVENTION

The field of the invention is orthotics.

BACKGROUND

The background description includes information that may be useful in understanding the present invention. It is not an admission that any of the information provided herein is prior art or relevant to the presently claimed invention, or that any publication specifically or implicitly referenced is prior art.

Neck problems are very common amongst humans due to a wide range of causes, including anything from poor posture to arthritis to broken bones. Neck braces can be essential to alleviate existing pain and prevent further injury, but are often too uncomfortable or immobilizing to wear for long periods of time. Moreover, many neck braces incorporate a one-size-fits-all model that is not tailored to the needs of individual wearers.

Some previous efforts have been directed toward design of neck braces that provide for improved comfort and tailoring to individual wearers. For example, U.S. Pat. No. 8,038,635 to Dellanno, titled "Forward Head Posture Correction Collar," filed on Dec. 16, 2008 describes a forward head position correction collar that allows a chin piece to be manually adjusted with respect to a shoulder collar assembly, in a vertical direction, and a horizontal axis extending in an anterior-posterior direction, in similar proportions. Unfortunately, Dellanno fails to provide for sufficient support of the occipital region of a wearer.

U.S. Patent Application Publication No. 2010/0185130 to Rizo Patron, titled "Custom Fit Cervical Collar," filed on Dec. 2, 2009 attempts to address some of the problems discussed above and describes a cervical collar that includes an occipital support region. However, the collar is designed to improve immobilization of the head and neck regions of a wearer in relation to the thorax, and does not provide for separate occipital support panels, movement of the occipital support for increased comfort, or a user friendly height adjustment mechanism that allows an adjustment of a vertical position of the occipital lobe support relative to the rear panel.

There are also various neck braces designed to be worn under a helmet to enhance the protection given by a helmet or protect against neck injuries while wearing a helmet, such as those described in European Patent No. 2117481 to Mazzarolo, filed on Jan. 3, 2007, International Patent Publication No. 2008/050307 to Leatt, filed on Oct. 26, 2007, and U.S. Pat. No. 7,846,117 to Leatt, filed on Jul. 17, 2007. Unfortunately, these braces also include many of the deficiencies described above, and have limited applications.

Thus, there is still a need for neck braces that provide improved comfort and modularity.

SUMMARY OF THE INVENTION

The inventive subject matter provides apparatus, systems and methods for neck braces having a rear brace with one or more occipital lobe supports and a height adjustment mechanism configured to allow adjustment of a vertical position of the one or more lobe supports with respect to the rear brace. The rear brace can be configured to wrap around a trapezius muscle of a wearer. In some aspects of the inventive subject matter, two occipital lobe supports can be coupled to at least one of a rear panel and a height adjustment mechanism. Preferred height adjustment mechanisms comprise a locking member and a moveable protrusion configured to move from a first position at least partially within a first notch to a second position at least partially within a second notch to thereby allow adjustment of a vertical position of the occipital lobe support relative to the rear panel.

In embodiments having two occipital lobe supports, it is contemplated although less preferred that a vertical position for each lobe support can be adjusted via a separate height adjustment mechanism. It is also contemplated that each of the lobe supports can be movably (e.g., pivotally, rotatably, etc.) coupled to the rear brace, such that the lobe support(s) can rotate and flex to contour to the back of a wearer's head. For example, the left occipital lobe support can have a first rotation (e.g., clockwise, counter-clockwise, etc.) or tilt (e.g., up, down, left, right, back, forth, a combination thereof, etc.) relative to the rear brace, and the right occipital lobe support can have a second rotation (e.g., clockwise, counter-clockwise, etc.) or tilt relative to the rear brace that is preferably independent from the first rotation. Such embodiments can be configured such that the lobe supports are each self-adjusting to the wearer's head.

It is contemplated that when any two components are removably or permanently coupled to one another, the two components can be movably coupled in a manner allowing rotation of at least one of the components about all axes (yawing, pitching and banking), and translation (i.e., sliding) in both transverse (i.e., lateral) and longitudinal directions. As used herein, the terms "movably coupled", "pivotally coupled" and "rotatably coupled" can each include, among other things, a coupling that allows a rotation (clockwise/counter-clockwise), and a tilting (back/forth/side to side).

A neck brace of the inventive subject matter can comprise various components, including for example, a front brace, chin support, rear brace, chest support, junction support, lobe support, thoracic support, or any other suitable component(s). Preferred braces advantageously have a modular construction, such that a doctor or other user could remove or replace one or more components of the brace or add an additional component based on an individual wearer's needs or preferences, often without requiring removal of the brace from the wearer.

In some preferred embodiments, the brace includes a front brace configured to removably couple with a rear brace via any suitable coupling mechanism (e.g., hook and loop fastener, buttons, snap fit, press fit, etc.). Exemplary front braces and chin supports are described in U.S. Pat. No. 7,141,031 to Garth, et al., and U.S. Pat. No. 7,674,234 to Calco, et al., each of which are incorporated by reference herein.

The neck brace can advantageously include one or more junction supports (e.g., cassettes, etc.), which can be configured to couple with a front or rear brace (or any other component) of the neck brace. In some embodiments, a junction support can be configured to couple with a junction support receiver of a rear panel. Such junction supports can comprise or couple with any suitable accessory, including for example, a belt, a back support, a strut, a chest supporting structure, or a realigning member. An exemplary realigning member is described in U.S. patent publ. no. 2010/0268139 to Garth, which is also incorporated by reference herein.

Various objects, features, aspects and advantages of the inventive subject matter will become more apparent from the following detailed description of preferred embodiments, along with the accompanying drawing figures in which like numerals represent like components.

DETAILED DESCRIPTION

One should appreciate that the disclosed techniques provide many advantageous technical effects including providing a wearer with one or more support mechanisms to support the back of the wearer's head, and in some embodiments are configured to rotate and flex to contour to the shape of the wearer's head and thereby support the wearer's head without any areas of undue pressure. One should also appreciate that the disclosed techniques provide a wearer with a versatile brace having a user friendly height adjustment mechanism.

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

Figure 1:
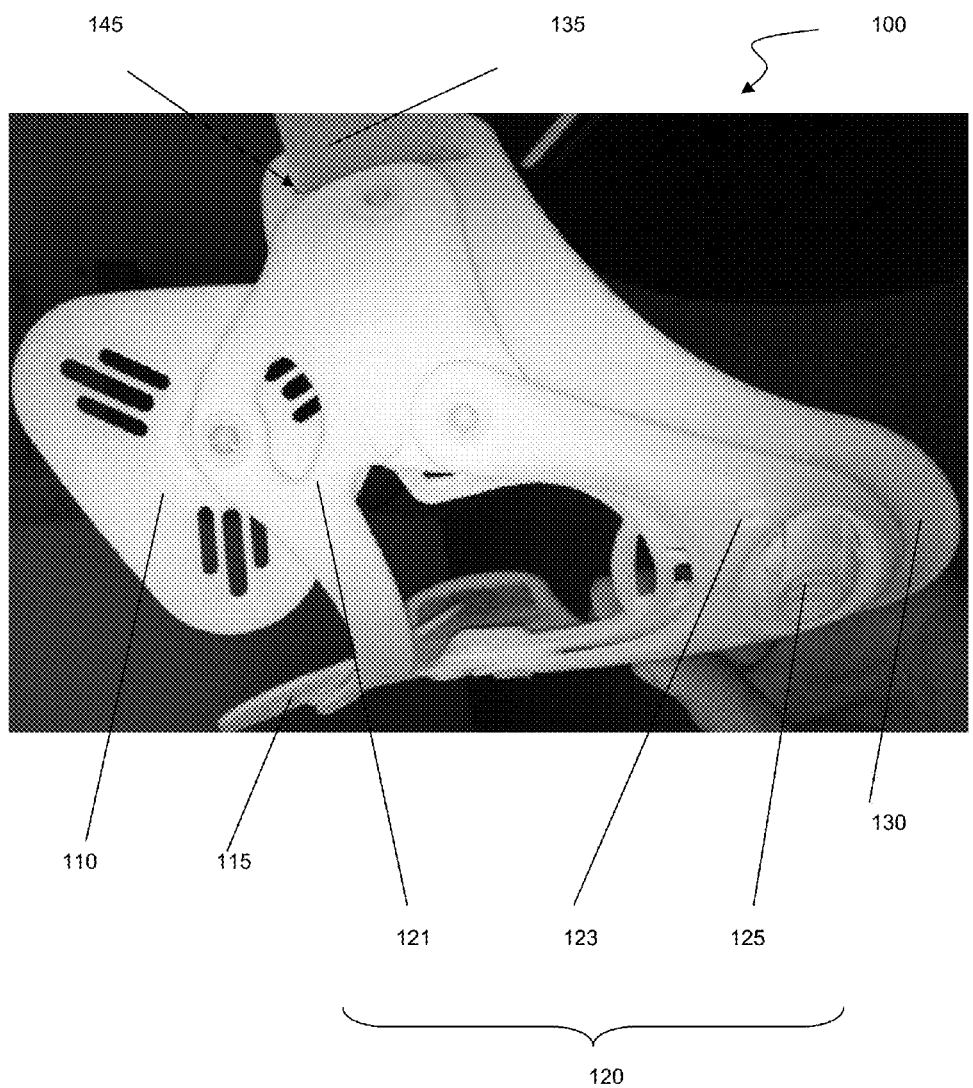
FIG. 1 shows one embodiment of a rear brace of the inventive subject matter.

FIG. 1 illustrates one embodiment of a rear brace 100 of the inventive subject matter. Rear brace 100 comprises first and second occipital lobe supports, 110 and 115, respectively, a rear panel 130, and an adjustment mechanism 120. Although two separate lobe supports are shown, it is contemplated that the rear brace could include a single lobe support configured to support both occipital lobes of a user. Adjustment mechanism 120 comprises an upper component 121 that is movably (e.g., rotatably, pivotally, etc.) coupled with lower component 123. Lower component 125 comprises a locking member 125 having a movable protrusion (not shown) configured to slidably fit at least partially within notches (not shown) of rear panel 130. In this manner, unintentional adjustment of the brace can advantageously be quickly and easily prevented.

Locking members of the inventive subject matter are further described below with reference to FIGS. 7A-7C.

Rear brace 100 further comprises a hook or loop fastener 135 that can be removably attached to (e.g., threaded through aperture 145 of) rear panel 130. It is also contemplated that a fastener can be fixedly attached to real panel 130. The rear brace's fastener could attach to any rear brace component (e.g., rear panel, attachment mechanism, lobe support, etc.) in any suitable manner. Suitable manners for attaching a fastener to a rear brace component includes, for example, the use of a zipper, an adhesive, threading through an aperture, a button, sewing onto the component, or stapling onto the component. Contemplated fasteners include, among other things, hook or loop, a button, a portion of a zipper, or any other fastener suitable for coupling a rear brace with another brace.

It is contemplated that rear brace 100 could be coupled to a front brace via a fastener of the front brace that is complementary to a rear brace's fastener. For example, a fastener complementary to a hook fastener can comprise a loop fastener. In this manner, the front brace (or other component) can be removably coupled to the rear brace 100 for increased modularity.

Figure 2A:
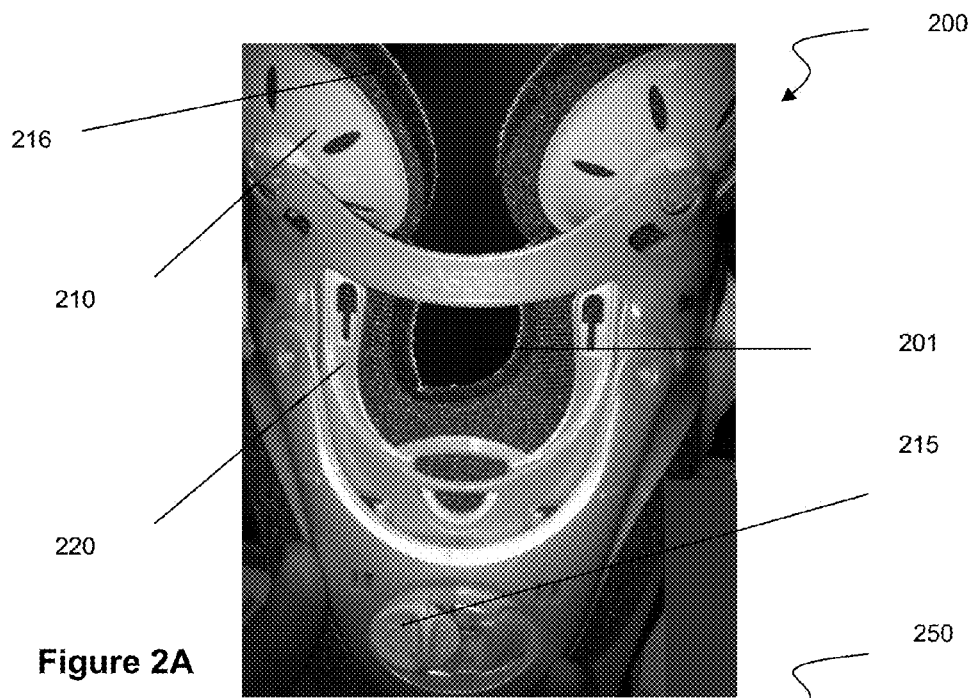
FIG. 2A shows an embodiment of a rear brace in a first configuration.
Figure 2B:
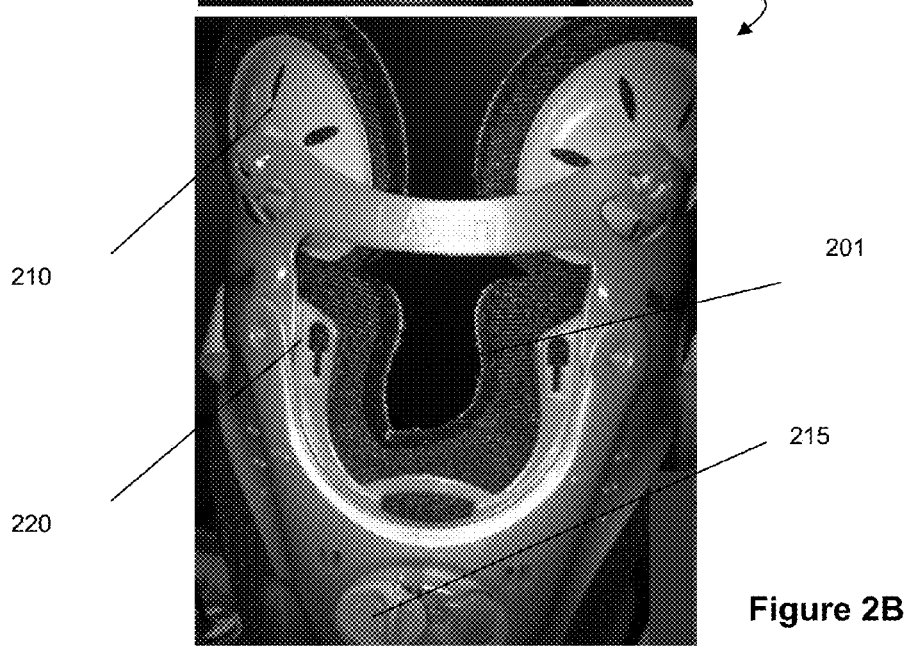
FIG. 2B shows an embodiment of a rear brace in a second configuration.

FIGS. 2A-2B show another embodiment of a rear brace of the inventive subject matter having two different configurations achieved via an adjustment mechanism of the brace. Configuration 200 shows occipital lobe support 210 in a low vertical position relative to rear panel 220. In this configuration, a sliding protrusion of locking member 215 is aligned vertically with the bottom-most notch of rear panel 220. Configuration 250 shows occipital lobe support 210 in a higher vertical position relative to rear panel 220, as evidenced by the differences in areas of access port 201 between configuration 200 and configuration 250. In configuration 250, the sliding protrusion of locking member 215 is aligned vertically with the upper-most notch of rear panel 220.

It is contemplated that a user can modify a vertical position of an occipital lobe support relative to a rear panel quickly and easily using the inventive subject matter. This can be true even where the user is a person wearing a brace of the inventive subject matter. For example a user can, in some embodiments, unlock a locking member and adjust a position of a sliding protrusion simply by utilizing the user's thumb or finger.

The brace can further include an access port (e.g., port 201) that advantageously allows a non-wearer of the neck brace to access a posterior portion of a neck of the wearer without requiring removal or movement of the brace. For example, through the access port, a doctor could access a surgical site along the spine. In addition, the access port could be left open to allow air-flow to cool the wearer, or could be utilized as a coupling port for another device or component, including, for example, a back attachment that couples to a lumbar support and a kyphosis support such as the one described in U.S. Patent Application Publication No. 2010/0268139.

The modular nature of the braces described herein of the inventive subject matter advantageously allows a user to add to, remove from, or otherwise modify a brace's functionality to adapt to a user's specific needs. For example, where a user desires improved occipital and lumbar support, a lumbar supporting member can be coupled to a coupling port of the brace's rear panel. Where a user desires kyphosis adjustment and a chin support, a simple rear panel (e.g., one having occipital lobe support removed, etc.) can couple with a front panel having a chin support, and also comprise a kyphosis supporting or adjusting member coupled with the coupling port.

Figure 3:
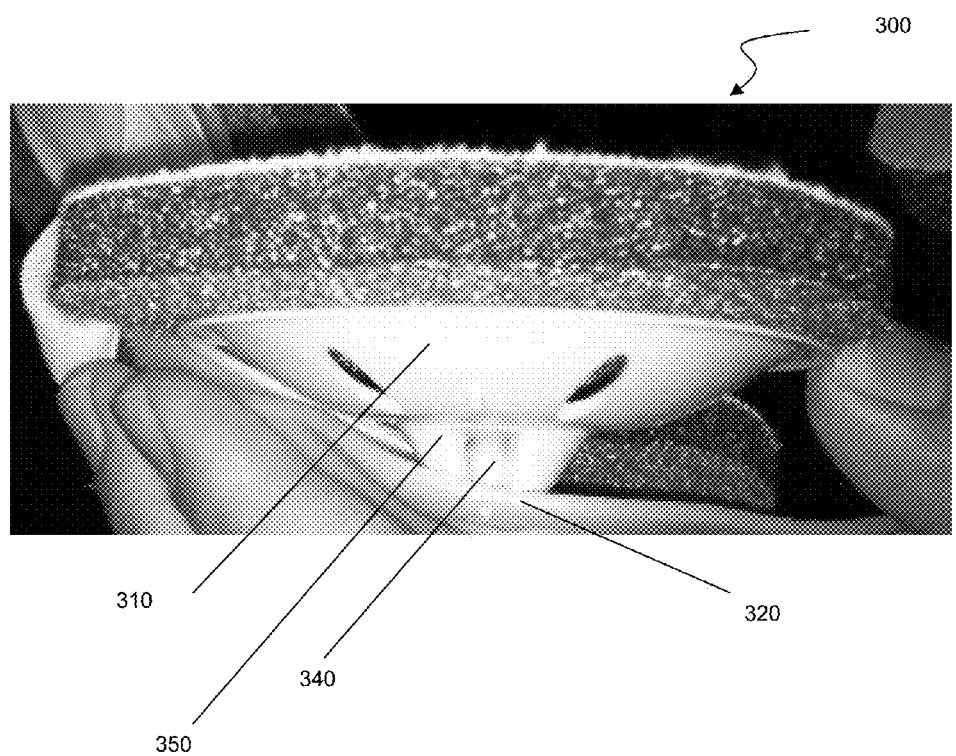
FIG. 3 is a top view of an occipital lobe support pivotally coupled with an upper component.

FIG. 3 shows an embodiment of an occipital lobe support 310 of rear brace 300. Occipital lobe support 310 comprises a receiver 350 that is configured to accept a protrusion 340 of adjustment mechanism 320. Protrusion 340 is rounded (e.g., spherical or egg shaped) and allows occipital lobe support 310 to rotate or pivot about protrusion 340 in all or substantially all directions. In some embodiments, an occipital lobe support can be fixedly attached to a portion of the rear brace.

It is contemplated that a rear brace of the inventive subject matter can comprise one or more occipital lobe supports that is sized and dimensioned to provide support to a wearer's occipital lobe. It is also contemplated that a rear brace of the inventive subject matter can comprise two or more occipital lobe supports that are each sized and dimensioned to provide support to a portion of a wearer's occipital lobe. Further, a rear brace can additionally or alternatively comprise one or more supports sized and dimensioned to support a temporal or parietal lobe of a wearer.

Lobe support 310 can be restricted by one or more rotation limiters, for example, a surface of adjustment mechanism 320 (or other component), or a protrusion of a component. Some rotation limiters can be configured to limit the rotation of at least one lobe support to no more than 90 degrees, 45 degrees, 20 degrees, 15 degrees, or even 10 or less degrees, or to limit a tilt of at least one lobe support to no more than 90 degrees, 45 degrees, 20 degrees, 15 degrees, or even 10 or less degrees. Of course, the specific limit of rotation could depend on various factors including the wearer, the size of the brace, and so forth.

Occipital lobe supports of all suitable shapes and sizes can be provided, including for example, a circular rounded disc, a circular flat disc, a triangular rounded disc, a triangular flat disc, a rectangular rounded disc, a rectangular flat disc, or any other suitable lobe support shape.

It is contemplated that each occipital lobe support can be movably (or fixedly) coupled to any portion of rear brace 300 in any suitable manner. For example, a portion of the rear brace 300 can comprise an aperture configured to accept a protrusion (e.g., a spherical protrusion, a mushroom shaped protrusion, an egg shaped protrusion, etc.) of an occipital lobe support.

Figure 4:
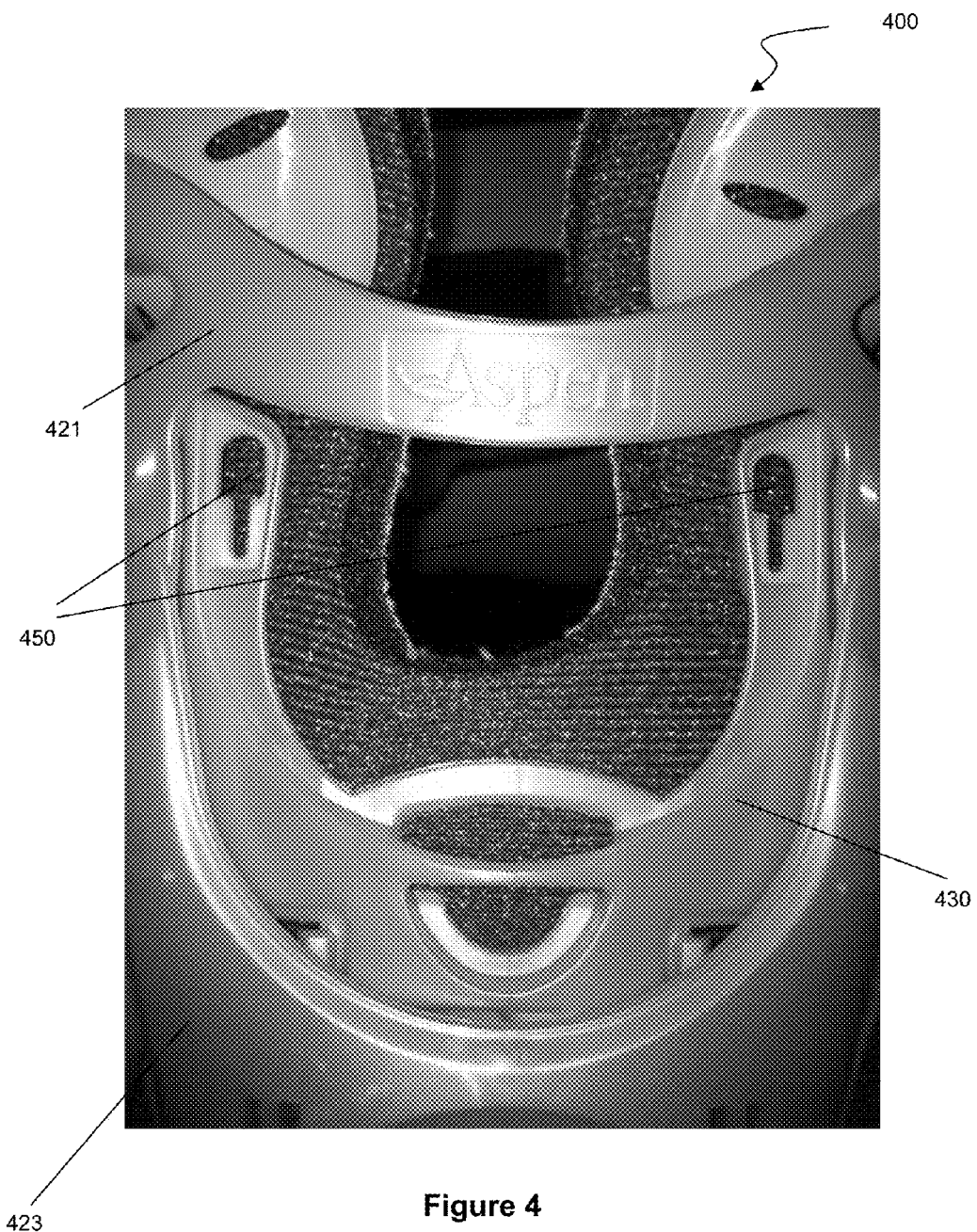
FIG. 4 shows a junction support receiver of the inventive subject matter.

FIG. 4 shows a rear brace 400 having a junction support receiver 450 configured to receive a modular component to expand the functionality of the brace to suit a wearer's needs. In some embodiments, one or more junction support receivers can be located on any portion of any component of a neck brace. Rear brace 400 has a rear panel 430 and an adjustment mechanism comprising an upper component 421 and a lower component 423. Rear panel 430 is partially exposed via an opening in upper component 421 and lower component 423. The exposed portion of rear panel 430 includes junction support receiver 450, which allows for receipt of a modular component as shown in FIG. 5.

Figure 5:
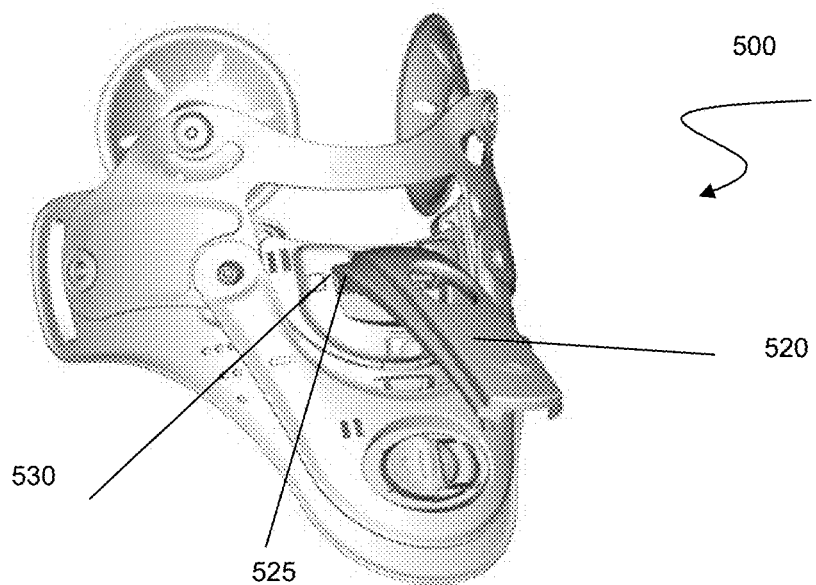
FIG. 5 shows one embodiment of a junction support of the inventive subject matter removably attached to a brace.

FIG. 5 is a perspective view of one embodiment of a rear brace 500 coupled to junction support 520. Rear brace 500 comprises a junction support receiver 530, which is sized and dimensioned to couple with junction support coupler 525 of junction support 520. It is contemplated that the junction support coupler 525 and junction support receiver 530 can couple with one another in any suitable manner, including for example, via a snap fit (e.g., cantilever snap fit, torsional snap fit, annular snap fit, etc.), twist fit, press fit, threading a strap through an aperture, carabiner, button, hook and loop fastener, magnet, clip, or any combination thereof.

One or more accessories, such as a belt, back support, strut, chest supporting structure, lumbar supporting member, chest supporting structure, realigner, or other modular component can be coupled with junction support 520 to allow a user to customize rear brace 500 to adapt to the needs of an individual wearer. For example, a junction support can be used to couple the brace with a strut to make a cervical-thoracic brace. As another example, a junction support could be used to couple the brace with a realigner to encourage realignment of the wearer's cervical curve, thoracic curve, lumbar curve of sacral curve. One possible realigner comprises a kyphosis adjustment mechanism as described in U.S. Patent Publication No. US 2010/0268139 to Garth.

In some embodiments, it is contemplated that an accessory itself can comprise couplers that are configured to couple with junction support receiver 530. In such embodiments, a junction support 520 would not be required.

It is also contemplated that a kit can be provided comprising junction support 520 and multiple accessories, each of which could be removably coupled with junction support 520. Such a kit could allow users to modify a neck brace of the inventive subject matter to best suit an individual wearer's unique preferences without purchasing an entirely new brace.

Figure 6A:
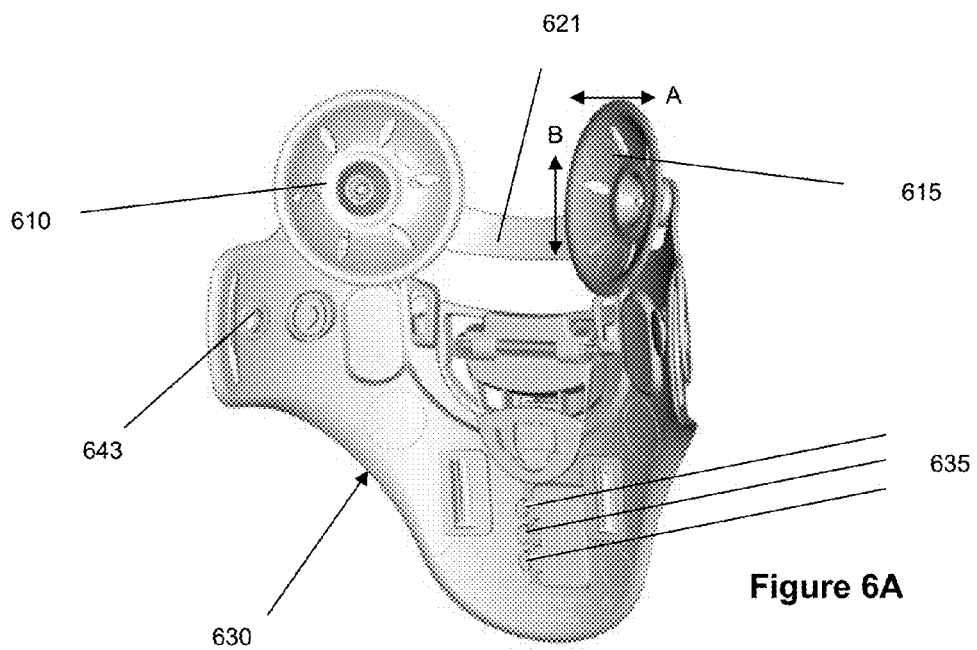
FIG. 6A is a perspective view of a rear brace of the inventive subject matter having an inner lining removed.
Figure 6B:
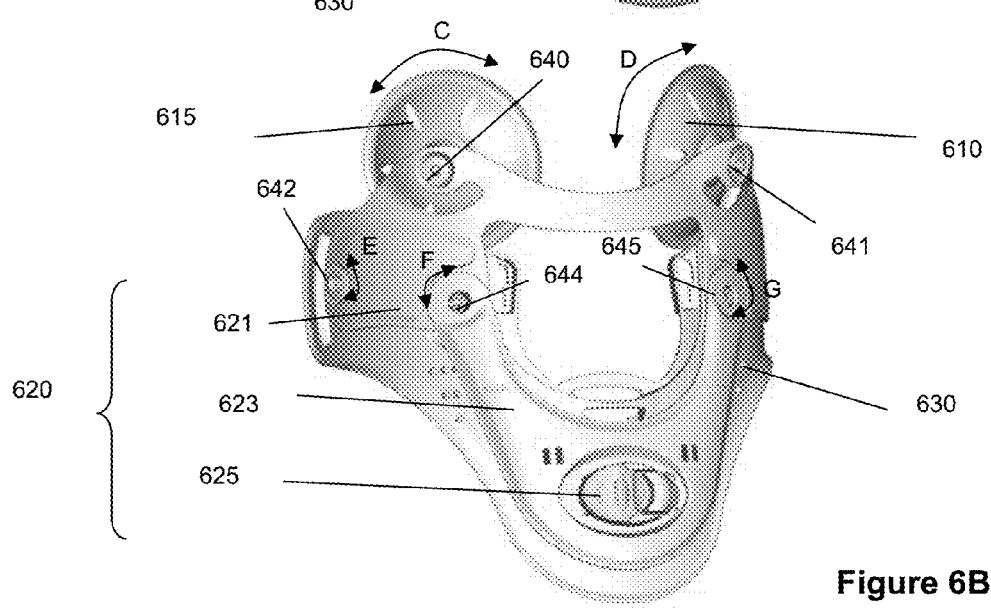
FIG. 6B is a different perspective view of the rear brace of FIG. 6A.

FIGS. 6A-6B are perspective views of another embodiment of the inventive subject matter. FIG. 6A is a perspective view of a back side of the rear brace (the side facing the wearer), and FIG. 6B shows a perspective view of a front side of the rear brace (the side facing away from the wearer). The brace comprises an upper component 621, lower component 623 and locking member 625, which collectively comprise adjustment mechanism 620. The brace further comprises first occipital lobe support 610 and second occipital lobe support 615, which are movably coupled with upper component 621. As described above, a brace of the inventive subject matter could alternatively comprise a single occipital lobe support.

Each of (1) the upper component and lower component, (2) occipital lobe support and upper component, and (3) upper component and rear panel can be movably coupled via ball snaps 640 and 641 or snap connectors 642-645. Ball snap 640 removably attaches second occipital lobe support 615 to upper component 621 in a manner that allows second occipital lobe support 615 to pivot or rotate about ball snap 640, relative to upper component 621 (e.g., in directions A, B, or C, etc.). As used herein, the term "ball snap" includes a fastener comprising a ball attached to one component of a neck brace, and a receiver counterpart on a different component that is configured to grab the ball and hold it until the components are pulled apart. Ball snap 641 removably attaches first occipital lobe support 610 to upper component 621 in a manner that allows first occipital lobe support 610 to pivot or rotate about ball snap 641, relative to upper component 621 (e.g., in directions D, etc.). Snap connectors 642 and 643 attaches upper component 621 to rear panel 630 in a manner that allows upper component to rotate or pivot about snap connectors 642 and 643 relative to rear panel 630 (e.g., in directions E, etc.). Snap connectors 644 and 645 attach upper component 621 to lower component 623 in a manner that allows lower component 623 to rotate or pivot about snap connectors 644 and 645, relative to upper component 621 (e.g., in directions F, G, etc.). As used herein, a "snap connector" includes a fastener comprising a mushroom shaped protrusion (e.g., a cap and a stem) attached to one component of a neck brace, and a receiver counterpart on a different component that is configured to snap fit with a cap portion of the protrusion, thereby attaching the two components to one another. It is contemplated that each of a ball snap and a snap connector can allow a permanent or removable attachment of two or more components of a neck brace.

Locking member 625 can comprise a movable protrusion (not shown) that is configured to move in and out of notches 635. This allows for preventing height adjustment when it is not desired. To adjust the vertical position of both occipital lobe supports 610 and 615, a user can simply and easily move the protrusion from a first notch to a second notch. Thus, for example, when the protrusion is moved out of the lowest notch and placed in one of the upper notches, lower component 623 or upper component 621 will move (e.g., pivot) relative to one another, and a vertical position of occipital lobe supports 615 and 610 can be adjusted (e.g., with a single movement of the protrusion, etc.) relative to rear panel 630. It is contemplated that once the protrusion slides into one of notches 635, it can be locking in place via locking member 625. This can be achieved via any commercially suitable mechanisms, including for example, a fastening (e.g., snap fitting, etc.) of locking member 625 with a locking member acceptor (such as locking member acceptor 726 shown in FIGS. 7A-7B).

In some embodiments, the locking member (or other portion of an adjustment mechanism) can comprise a pinion having protrusions and one or more racks having notches, each notch sized and dimensioned to receive at least a portion of a pinion protrusion. One example of such a rack and pinion adjustment mechanism is described in U.S. Pat. No. 7,674,234 to Calco. It should be noted that in some embodiments, a movement of a protrusion from one notch to another notch can cause simultaneous adjustment of a vertical position of one or more occipital lobe supports.

Figure 7A:
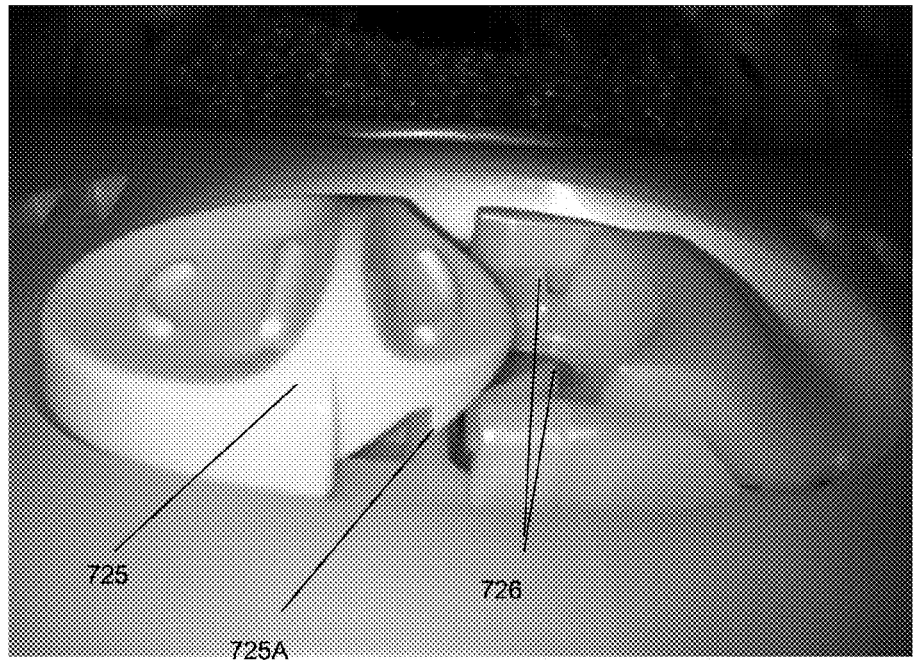
FIG. 7A is a close up view of a locking member acceptor.
Figure 7B:
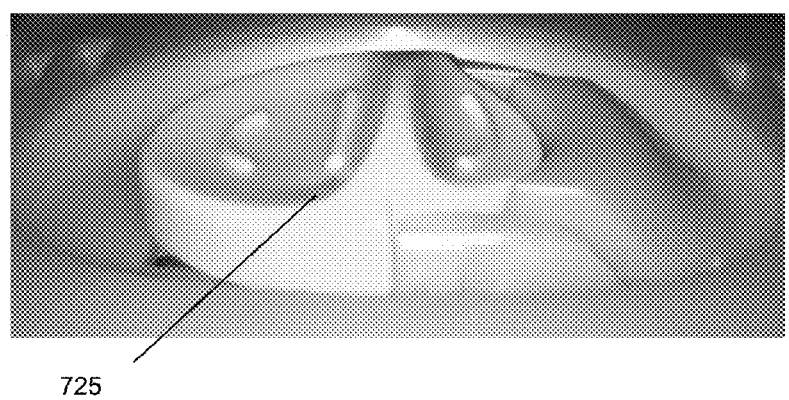
FIG. 7B is a close up view of a locking member in a locked position.

FIGS. 7A-7B show a locking member 725 and locking member acceptor 726. Locking member 725 comprises ridge 725A, which is configured to snap fit or otherwise mate with locking member acceptor 726 to lock the position of a protrusion within a notch. FIG. 7A shows a locking member that is in an unlocked position, while FIG. 7B shows locking member in a locked position, with locking member 725 snap fit with locking member acceptor 726.

Locking members of the inventive subject matter can alternatively comprise, for example, a spring biasing mechanism such that locking member is biased towards a locked position. In such embodiments, locking member can be moved away from its biased locked position in a first notch, be moved upwards or downwards, and then released back to its biased locked position in a different notch. Moreover, a locking member can comprise a protrusion having a hook (or other bent) shape configured to move in and out of two or more notches having a divot-shaped portion. In such embodiments, a locking member can be used to lift up the protrusion out of the divot-shaped portion, and then move the protrusion from one notch to another notch having a divot-shaped portion. In this manner, the hook shaped portion and the divot-shaped portion could act as a locking mechanism.

Figure 8A:
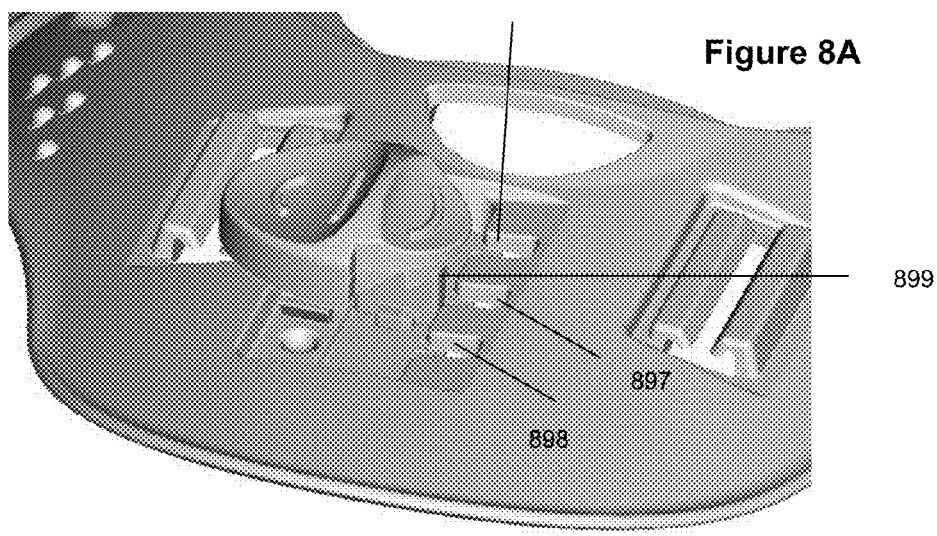
FIG. 8A shows one embodiment of a slidable protrusion and notches of the inventive subject matter.
Figure 8B:
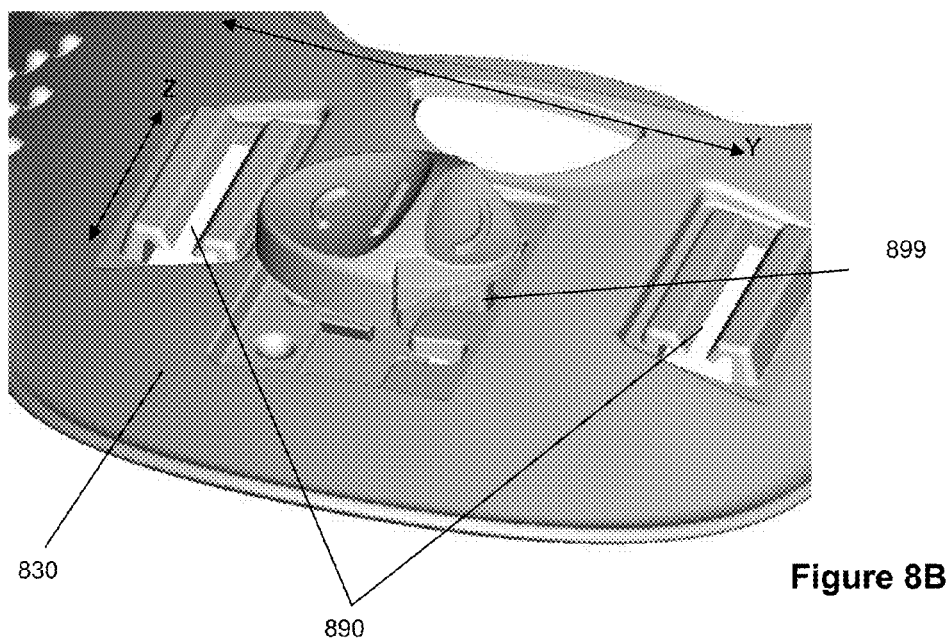
FIG. 8B shows the slidable protrusion of FIG. 8A slidably fit in a notch of a rear panel.

FIGS. 8A-8B show a rear panel of the inventive subject matter interacting with a slidable protrusion of a locking member. Protrusion 899 composes a locking mechanism and is configured to slide in and out of first notch 896, second notch 897, and third notch 898. It is contemplated that slidable protrusion and notches 896-898 can allow a user of a neck brace of the inventive subject matter to quickly and easily adjust a vertical position of one or more occipital lobe supports with a single adjustment.

Rear panel 830 can further include guiding mechanism 890 to stabilize a movement of a lower component (or other component) relative to the rear panel. An adjustment mechanism of a brace can comprise a prominence that is configured to slide along guiding mechanism 890 in directions Z. This guiding mechanism 890 can keep an adjustment mechanism from moving side to side in directions Y. In some other embodiments, a guiding mechanism can keep an adjustment mechanism from unintentionally moving in an up or down direction, diagonal direction, or any other possible direction.

It is contemplated that a neck brace of the inventive subject matter can comprise 1, 2, 5, 10, or even 20 or more components. It is also contemplated that each component can be of any suitable shape and size. For example, a rear brace can be sized and dimensioned to wrap around an entire neck of a wearer. As another example, a rear brace can be sized and dimensioned to wrap around a neck, chin, and trapezius muscle of a wearer. As yet another example, a front brace can be configured to wrap around a chest, neck and lower back of a wearer.

Each component can be made of any suitable material(s), including for example, a foam, a gel, a silicon, a plastic, a cotton, a Nylon, or any other suitable material. Thus, it is contemplated that a rear brace can be made entirely of plastic(s), while a padding that removably attaches to an interior side of the rear brace is made entirely of cotton, foam and polyester (e.g., a cotton lining and a polyester lining sandwiching a foam layer.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A neck brace having a rear brace, the rear brace comprising:
   a rear panel having an outer surface with first and second notches;
   a height adjustment mechanism coupled to the rear panel;
   first and second occipital lobe supports separately coupled to the height adjustment mechanism;
   wherein the height adjustment mechanism comprises an upper component movably coupled to a lower component, and a movable protrusion coupled to the lower component;
   wherein the lower component overlies at least a portion of the rear panel such that a back side of the lower component faces a front side of the rear panel;
   wherein the movable protrusion is positioned on the back side of the lower component, and wherein the first and second notches are positioned on the front side of the rear panel where the back side of lower component faces the front side of the rear panel, and wherein the first and second notches are each sized and dimensioned to allow receipt of at least a portion of the protrusion; and
   wherein the height adjustment mechanism is configured to simultaneously allow adjustment of a vertical position of each of the first and second occipital lobe supports relative to the rear panel when the at least the portion of the protrusion moves from within the first notch to within the second notch.

2. The brace of claim 1, wherein the rear panel further includes a junction support receiver.

3. The brace of claim 2, wherein the junction support receiver is configured to couple the rear panel with a junction support.

4. The brace of claim 3, wherein the junction support comprises a realigning member.

5. The brace of claim 3, wherein the junction support comprises a belt.

6. The brace of claim 3, wherein the junction support comprises a back support.

7. The brace of claim 3, wherein the junction support comprises a strut.

8. The brace of claim 3, wherein the junction support comprises a chest supporting structure.

9. The brace of claim 1, wherein the adjustment mechanism couples the first occipital lobe support to the rear panel, and wherein the adjustment mechanism is pivotally coupled to the rear panel.

10. The brace of claim 9, wherein the first and second occipital lobe supports are pivotably coupled to the adjustment mechanism.

11. The brace of claim 9, further comprising an access port located between the upper component and the rear panel that allows access to a posterior portion of a neck of a wearer.

12. The brace of claim 1, wherein the rear panel further comprises a third notch, and wherein the third notch is sized and dimensioned to allow receipt of at least the portion of the protrusion.

13. The brace of claim 1, further comprising a locking member, wherein the locking member includes the movable protrusion.

14. The brace of claim 1, wherein the first and second occipital lobe supports are movably coupled to the adjustment mechanism.

15. The brace of claim 1, further comprising a rack, wherein the movable protrusion composes a pinion, and wherein the rack comprises each of the first and second notches.

16. A neck brace, comprising:
   a rear panel configured to wrap around at least a portion of a trapezius muscle of a wearer;
   a first occipital lobe support coupled to the rear panel via an adjustment mechanism such that the first occipital lobe support includes a receiver sized and dimensioned to accept a first protrusion of an adjustment member, and wherein the first occipital lobe support can pivot about the adjustment member protrusion to contour to a back of the wearer's head when worn;
   wherein the adjustment mechanism comprises a second protrusion and first and second notches, each of the first and second notches being sized and dimensioned to receive at least a portion of the second protrusion; and
   wherein the adjustment mechanism is configured to adjust a vertical position of the first occipital lobe support relative to the rear panel when the second protrusion is shifted from the first notch to the second notch.

17. The brace of claim 16, further comprising a second occipital lobe support coupled to the rear support via the adjustment mechanism.

18. The brace of claim 17, wherein the adjustment mechanism is further configured such that a single adjustment to the adjustment mechanism operates to simultaneously change a vertical position of both the first and second occipital lobe supports relative to the rear panel.

19. The brace of claim 16, wherein the adjustment mechanism further comprises a lock configured to prevent movement of the second protrusion.

20. A neck brace, comprising:
   a rear panel configured to wrap around at least a portion of a trapezius muscle of a wearer;
   an adjustment mechanism coupled to the rear panel and comprising an upper component movably coupled to a lower component;
   an occipital lobe support coupled to the upper component via a fastener including a first protrusion and a receiver sized and dimensioned to accept the protrusion, and wherein the occipital lobe support can pivot relative to the upper component about the fastener to contour to a back of the wearer's head when worn; and
   wherein the lower component of the adjustment mechanism includes a locking member including a movable second protrusion that is sized and dimensioned to insert into and retract from a plurality of vertically arranged notches located on a portion of a front side of the rear panel that a portion of a back side of the lower component faces, and wherein moving the second protrusion from a first of the plurality of vertically arranged notches to a second of the plurality of vertically arranged notches adjusts a vertical position of the occipital lobe support relative to the rear panel.

* * * * *